United States Patent [19]
Bader et al.

[11] 4,196,132
[45] Apr. 1, 1980

[54] CONTINUOUS FLOW PROCESS FOR THE PREPARATION OF O-CHLORANIL FROM TETRACHLOROCATECHOL

[75] Inventors: Fredric G. Bader, Portage; Howard J. Burke, Kalamazoo, both of Mich.

[73] Assignee: The Upjohn Company, Kalamazoo, Mich.

[21] Appl. No.: 932,714

[22] Filed: Aug. 11, 1978

[51] Int. Cl.$^2$ .............................................. C07C 45/16
[52] U.S. Cl. ........................ 260/396 R; 260/586 R; 568/776; 568/765
[58] Field of Search ........... 260/586 R, 586 P, 396 R; 568/776

[56] References Cited

U.S. PATENT DOCUMENTS 2,920,082  1/1960  Rocklin ............................ 260/396 R

OTHER PUBLICATIONS

Sah et al., "Arzneimittel Forsch.", 11:27–33 (1961).
Jackson et al., "Am. Chem. J." 38:127–175 (1907).
Jackson et al., "Am. Chem. J.", 39:493–505 (1908).
Sah et al., "Chem Ab.", 57:164669 (1972), [Arzneimittel Forsch., 11:27–33 (1961)].

Primary Examiner—Norman Morgenstern
Attorney, Agent, or Firm—Hans L. Berneis; Robert A. Armitage

[57] ABSTRACT

3,4,5,6-Tetrachloro-3,5-cyclohexadiene-1,2-dione (o-chloranil), a valuable organic oxidant used particularly in the photographic industry, has now been found to be synthesizable by an improved, continuous flow process from catechol.

5 Claims, 1 Drawing Figure

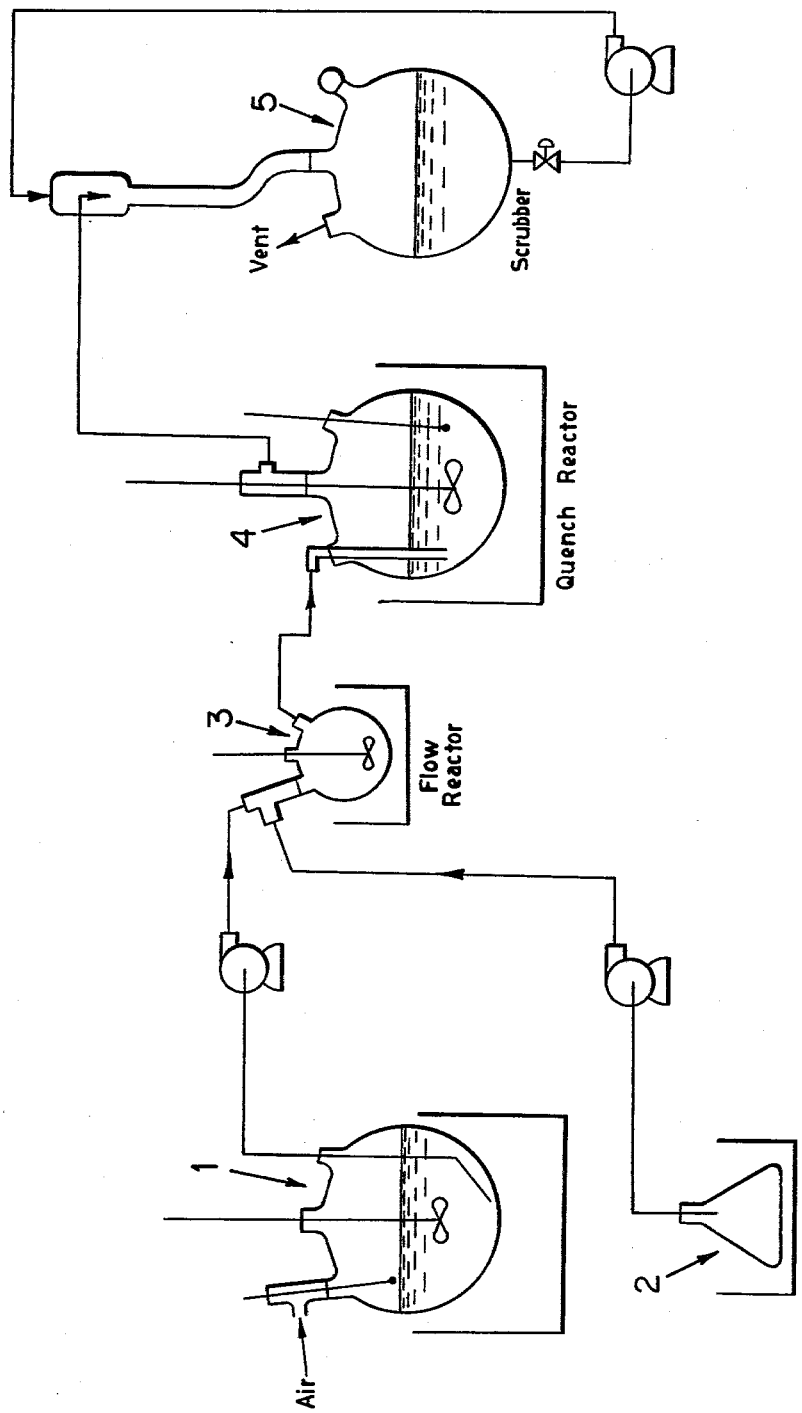

CONTINUOUS FLOW PROCESS FOR THE PREPARATION OF O-CHLORANIL FROM TETRACHLOROCATECHOL

BACKGROUND OF THE INVENTION

Field of the Invention

The present invention is directed to a new, improved, continuous process for the manufacture of 3,4,5,6-tetrachloro-1,2-cyclohexadiene-1,2-dione (III, o-chloranil), from catechol I.

The process can be illustratively represented by the following scheme:

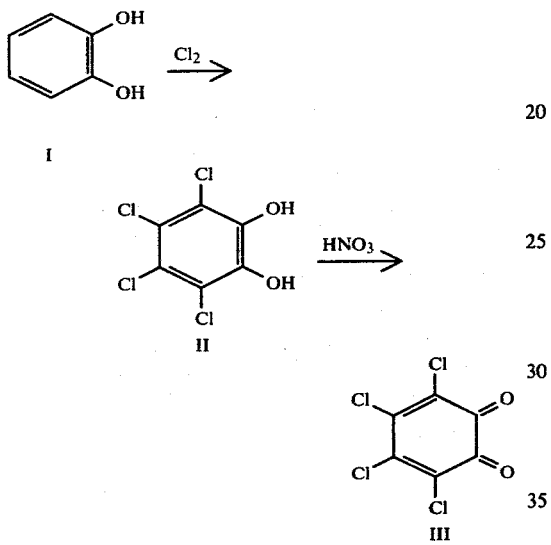

This process was carried out in the past as a batch process as to step II→III (step I→II still is a batch process) providing at best up to 62% yield (I→III) and sometimes as low as 47%.

The present process I→III can provide more than 80% yield.

Besides the advantages of higher yields, the new technology was also found to be much safer. When the step II→III is run as a batch process, NO and $NO_2$ gases are produced by the disproportionation reaction of the by-product, nitrous acid. These gases accumulate to produce a super-saturated solution which can suddenly release the dissolved gases with sufficient violence to throw the reaction mixture out of the reaction vessel. In the new flow method, the toxic $NO_x$ gas development is much decreased and presents no problems. The chlorination step (first step) of the process of this invention is carried out by reacting catechol in solution or suspension in an organic solvent with gaseous chlorine. The solvents used for this reaction comprise glacial acetic acid, propionic acid, tetrahydrofuran, toluene, ethyl acetate, carbon tetrachloride, methylene chloride, chloroform, or like solvents, bearing in mind that the solvent must be inactive during chlorination. Glacial acetic acid is the preferred suspension agent at the temperatures of the reaction. The chlorine gas may be used in stoichiometric amounts or amounts slightly larger but not more than 10% over the calculated amount. The chlorine addition should be stepwise or in a steady flow and not all at once. During the reaction the temperature rises considerably and cooling is necessary. The reaction can be carried out between 14° C. and 40° C. and is preferably started between 14° C. and 20° C. with the high temperatures kept under 30° C.

After all chlorine has been reacted, the slurry of tetrachlorocatechol and suspension agent is further diluted with an organic solvent or suspension agent, e.g., carbon tetrachloride, chloroform, methylene chloride, or the like, and used directly in the continuous oxidation step II→III. The continuous oxidation involves a system of two container vessels for the reactants, a flow reactor, a quench reactor, and a scrubber. The FIGURE shows a laboratory arrangement as used for the Example below. Flask 1 is the storage for the tetrachlorocatechol slurry; flask 2 is the storage for concentrated nitric acid. Both flasks are cooled to between 0° C. and 5° C., e.g., by an icebath. Each flask is connected individually to the flow reactor 3 with pumps moving the reactants along at the desired rates. In reactor 3 (at between −2° and 6° C., with +2° to 5° C. preferred) the actual oxidation takes place giving o-chloranil.

The product produced in vessel 3, nitrous acid, and possibly some produced nitrogen oxide is transported to the quench reactor 4, in which the product is collected. The nitrous acid is decomposed with sulfamic acid which is contained in the quench reactor 4:

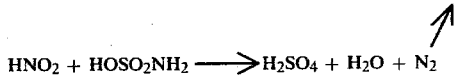

The gases, nitrogen and perhaps some nitrogen oxides, pass from quench reactor 4 to the scrubber 5 which is charged with an alkali hydroxide solution, usually sodium hydroxide. The alkali hydroxide solution will bind any nitrogen dioxide. Air is injected into the gas stream prior to the scrubber to oxidize any NO to $NO_2$. A vent connected to the scrubber 5 will allow the nitrogen formed in vessel 4 to escape. The various vessels (at least 1, 3 and 4) are also equipped with means to produce agitation and vessels 1 and 4 at least are provided with means to read the temperatures. Besides o-chloranil, nitrous acid ($HNO_2$) is produced which, being unstable, decomposes to nitrogen oxide and dioxide:

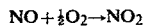

In a batch system the nitrogen oxides are not initially produced. After a time delay, however, in which nitrous acid accumulates, a sudden gas evolution takes place which produces excessive foaming, increased pressure, and can blow the reaction mixture from the vessel.

Since in the above flow system the holding time in the reactor III (between 0.4 to 2 minutes) is short, only a small amount of gas production takes place. Thus, the flow system is considerably safer than the batch oxidation.

The above schematic arrangement is the basic apparatus order used in the example, part B, and can be used with appropriate larger vessels for quantity production.

The following example is illustrative of the process of this invention but should not be construed as limiting.

EXAMPLE

(A) Tetrachlorocatechol from Catechol

A solution was prepared from 150 g of catechol in 675 ml of glacial acetic acid and cooled by means of an ice bath. Chlorine gas was sparged through this mixture at a rate of 3.68 g/minute for 100 minutes, followed by a stream of chlorine at a rate of 0.81 g/minute. The total chlorine fed was 428.7 g. The reaction temperatures varied between 14° C. and 24° C.

During the chlorine addition, 75 minutes from the beginning of the addition, solids started to precipitate. After the chlorine addition was complete, 900 ml of methylene chloride was added and the mixture cooled to 3° C. The reaction mixture, a slurry of mostly tetrachlorocatechol, was used for the next step.

(B) o-Chloranil from Tetrachlorocatechol

A system was constructed in which the slurry of tetrachlorocatechol (of (A) above) was transported in a steady flow into a reactor vessel (see FIGURE) which, at the same time, was receiving a constant stream of concentrated ice-cooled nitric acid (about 69-71%).

The tetrachlorocatechol slurry was pumped to said flow reactor at a rate of 88.75 ml/minute and nitric acid (70%) was pumped to the said flow reactor at a rate of 7.50 ml/minute (72% excess). Thus, the total flow into the reactor was 96.25 ml/minute. The flow reactor volume was 50 ml and the reactor holding time was 0.52 minutes [vol./flow rate].

From the flow reactor the material passed into a larger quench reactor (5 liter) containing 900 ml of water and 132 g of sulfamic acid ($HOSO_2NH_2$). The quench reactor is cooled by means of an ice bath to an initial temperature of about 2° C. Excess gases formed during the oxidation reaction (NO, $NO_2$, $N_2O_4$) and quench reaction ($N_2$) were allowed to escape to a scrubbing vessel in which the various nitrogen oxide gases could be absorbed by a 25% aqueous sodium hydroxide solution.

When the flow reaction was complete, the tetrachlorocatechol-slurry flask was rinsed with 225 ml of methylene chloride which was pumped through the flow reactor. The remaining contents of the flow reactor were poured into the quench reactor and all pumps were turned off.

During the flow reaction, the quench reactor temperature went from 2° C. to a maximum temperature of 25° C. Large volumes of gas came off from the quench reactor. No $NO_2$ gas was detected by sight or smell in the quench reactor or the scrubber.

When the quench reactor had been cooled to 5° C., the contents were poured into a 4 liter separatory funnel and the bottom methylene chloride phase containing o-chloranil was separated from the aqueous-acetic acid phase. The aqueous phase was backwashed with 200 ml of fresh methylene chloride. The combined methylene chloride phases were washed with 2×900 ml of 5° C., 5% sodium chloride-water solution. Each sodium chloride wash was backwashed with 100 ml of fresh methylene chloride.

The final methylene chloride-o-chloranil solution was evaporated on a rotary vacuum evaporator at room temperature. The yield of crude o-chloranil was 339.05 g (101.2% of theory).

The crude o-chloranil is dissolved in 600 ml of carbon tetrachloride at 60° C. and cooled to 0° C. for 4 hours to crystallize the chloranil which is filtered on a glass filter, washed with 100 ml of 0° C., carbon tetrachloride, sucked dry and dried in a vacuum oven at room temperature. The first crop yield of o-chloranil was:

Yield: 261.12 g of o-chloranil (77.94%)
M.P.: 128°–130° C.
Titration: 99.3%

The mother liquors were heated to 60° C., evaporated to a volume of 200 ml., cooled overnight to room temperature, and cooled to 0° C. for one hour. The resulting slurry was filtered on a glass filter, washed with 100 ml of 0° C. carbon tetrachloride, sucked dry and dried in a vacuum oven at room temperature. The second crop yield of o-chloranil was:

Yield: 13.58 g of o-chloranil (4.05%)
M.P.: 125°–127.5° C.
Total Yield: 274.70 g (81.99%)

Five pilot plant runs with 18.7 to 19.5 kg of catechol were carried out. The maximum yield of o-chloranil (in the two steps: catechol→tetrachlorocatechol→chloranil) was 70.09%. Commercial catechol, about 99% pure, was used in the pilot plant runs.

The continuous method shown in the disclosed example can be compared to the best batch example run, described below:

Chloranil by Batch Method 50 g of CP grade catechol (Crown Zellerbach) was dissolved in 225 ml of glacial acetic acid in a 1 liter round bottom flask. A 1/1 mixture of $Cl_2/N_2$ was passed through the catechol solution for 3 hours 15 minutes until a redox potential of 9.8 was reached. After chlorination for 1 hour 40 minutes, white solids (tetrachlorocatechol) precipitated from the reaction mixture. The temperature during the chlorination ranged from 20° to 40° C.

At the end of the chlorination, the chlorination reaction mixture was sparged with nitrogen for 40 minutes. Methylene chloride (300 ml) was then added and the reaction mixture (a slurry of white solids) was cooled to +5° C. The tetrachlorocatechol slurry was oxidized by adding a mixture of 58 ml of 35% nitric acid in which 22 g of sulfamide had been dissolved. The acid addition time was 20 minutes which was as fast as it could be added due to the large volume of gas produced.

At the end of the oxidation, the reaction mixture was extracted with 3×300 ml of 5% of sodium chloride-water solution. The product remained with the methylene chloride phase and the acetic acid was washed out with the aqueous phase. Each aqueous phase was backwashed with 50 ml of methylene chloride. All washes were performed at ~5° C.

The methylene chloride-o-chloranil solution was dried to remove water by filtering it over a bed of anhydrous sodium sulfate. The methylene chloride product solution was flash dried in a roto-vac evaporator.

The dry crude o-chloranil was dissolved in 225 ml of carbon tetrachloride, heated to 75° C. and cooled over 4 hours to 0° C. During the cooling, the o-chloranil crystallized out. The cooled product solution was filtered on a sintered glass filter and washed with 100 ml of 0° C. carbon tetrachloride to give 69.36 g (62.1% of theory) of o-chloranil of melting point 126.5° C. to 128.5° C.

A second crop from the mother liquors was too impure to be useful.

Other comparisons were made as follows:

A. A batch of tetrachlorocatechol (TCC) slurry, prepared as described in part A of the Example, was divided in approximately two equal parts, one of 908 g slurry and one of 927 g slurry. The 908 g of TCC was batch oxidized with nitric acid providing a yield of 63.42% (referred to the original catechol) and the flow-oxidized batch of 927 g yielded 88.20% (referred to the original catechol).

B. In a similar comparison, from 1000 g of TCC slurry a yield of 47.78% of o-chloranil was obtained in the batch process, while from 1035 g of TCC slurry o-chloranil was obtained in 81.15% yield in the continuous process. The TCC slurry in this comparison experiment, like under A, was obtained from the same batch.

The purity of chloranil from the continuous processes was in both comparison tests superior to that obtained in the batch process.

We claim:

1. An improved process for the production of o-chloranil, which comprises (1) reacting, in a batch process, catechol with an excess of up to 10% of the calculated stoichiometric amount of chlorine at 14° to 40° C. in suspension in an organic, non-chlorinating solvent to provide a slurry of tetrachlorocatechol (II):

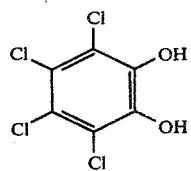

II (2) oxidizing said slurry in a flow reactor arranged for a holding time of 0.4 to 2 minutes with concentrated nitric acid at about 0° to 5° C. to obtain o-chloranil III

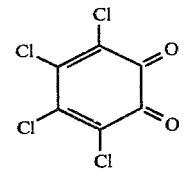

III while decomposing with sulfamic acid amide the produced nitrous acid.

2. The process of claim 1 wherein the chlorination is carried out between 14° and 20° C.

3. The process of claim 1 wherein the flow reactor is arranged for a holding time of 0.5 to 1.5 minutes.

4. An improved process for the production of o-chloranil III:

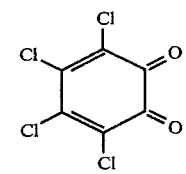

III which comprises adding into a flow reactor concentrated nitric acid at a temperature from 0° to 50° C. and separately a slurry of tetrachlorocatechol II

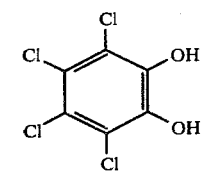

II in a non-chlorinatable organic solvent, said slurry being cooled to from 14° to 20° C. to produce o-chloranil III above while decomposing the formed nitrous acid with sulfamic acid amide in a quench reactor.

5. The process of claim 4 wherein tetrachlorocatechol is slurried in glacial acetic acid and methylene chloride.

* * * * *

UNITED STATES PATENT OFFICE
CERTIFICATE OF CORRECTION

Patent No. 4,196,132          Dated 1 April 1980

Inventor(s) F.G. Bader, et al.

It is certified that error appears in the above-identified patent and that said Letters Patent are hereby corrected as shown below:

Column 6, line 10, "sulfamic acid amide the" should read -- sulfamic acid the --.
Column 6, line 41, "sulfamic acid amide in" should read -- sulfamic acid in --.

Signed and Sealed this

*Second* Day of *November 1982*

[SEAL]

Attest:

Attesting Officer

GERALD J. MOSSINGHOFF

*Commissioner of Patents and Trademarks*